United States Patent
Drewes et al.

(10) Patent No.: US 7,153,651 B1
(45) Date of Patent: *Dec. 26, 2006

(54) FLOW-THROUGH OPTICAL ASSAY DEVICES PROVIDING LAMINAR FLOW OF FLUID SAMPLES, AND METHODS OF CONSTRUCTION THEREOF

(75) Inventors: Joel A. Drewes, Woodbridge, VA (US); Gregory R. Bogart, Raritan, NJ (US); Jeffrey B. Etter, Boulder, CO (US); Jeffrey W. Steaffens, Lafayette, CO (US); Rachel M. Ostroff, Westminster, CO (US); Mark Crosby, Boulder, CO (US)

(73) Assignee: Inverness Medical - Biostar, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/950,963

(22) Filed: Oct. 15, 1997

Related U.S. Application Data

(63) Continuation-in-part of application No. 08/742,255, filed on Oct. 31, 1996, now abandoned.

(51) Int. Cl.
*C12Q 1/68* (2006.01)
*C12M 1/00* (2006.01)
*G01N 15/06* (2006.01)

(52) U.S. Cl. .............. 435/6; 435/283.1; 435/287.2; 422/68.1; 422/82.05

(58) Field of Classification Search ............. 435/6; 436/518; 427/162, 164, 163.4, 167; 310/313
See application file for complete search history.

(56) References Cited

U.S. PATENT DOCUMENTS

| | | | | |
|---|---|---|---|---|
| 4,632,901 A | | 12/1986 | Valkirs et al. ............... 435/5 |
| 4,685,534 A | * | 8/1987 | Burstein et al. ........... 181/251 |
| 4,775,636 A | | 10/1988 | Moeremans et al. ........ 435/518 |
| 4,818,710 A | | 4/1989 | Sutherland et al. |
| 4,849,340 A | * | 7/1989 | Oberhardt ................... 435/13 |
| 4,931,384 A | | 6/1990 | Layton et al. |
| 5,075,078 A | | 12/1991 | Osikowicz et al. ........... 422/56 |
| 5,167,823 A | | 12/1992 | Leighton et al. ............ 210/637 |
| 5,200,312 A | | 4/1993 | Oprandy ...................... 435/5 |
| 5,232,835 A | | 8/1993 | Litman et al. ............ 435/7.93 |
| 5,273,788 A | | 12/1993 | Yu |

(Continued)

FOREIGN PATENT DOCUMENTS

EP   0 343 826   11/1989

(Continued)

OTHER PUBLICATIONS

Brecht et al., A direct optical immunosensor for atrizine detection, Analytica Chimica Acta, vol. 311, 289-299, 1995.*

(Continued)

*Primary Examiner*—BJ Forman
(74) *Attorney, Agent, or Firm*—Swanson & Bratschun

(57) ABSTRACT

An optical assay device for the detection of an analyte of interest in a sample comprising a support containing channels, an optically functional layer positioned on the support such that the optically functional layer and the support allow for laminar flow of the sample through layers of the device, an attachment layer positioned on the optically functional layer, and an analyte specific receptive layer positioned on the attachment layer.

40 Claims, 3 Drawing Sheets

Figure 1:
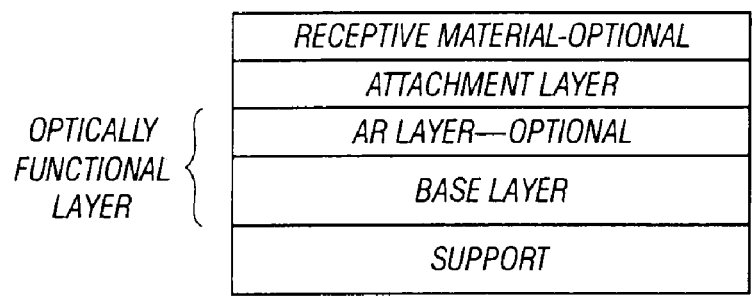

OPTICALLY FUNCTIONAL LAYER
SUPPORT WITH CHANNELS

OPTICALLY FUNCTIONAL LAYER CONTAINING CHANNELS
POROUS SUPPORT

U.S. PATENT DOCUMENTS

| | | | |
|---|---|---|---|
| 5,358,880 A | 10/1994 | Lebby et al. | 437/23 |
| 5,393,658 A | 2/1995 | Olsen | 435/7.36 |
| 5,395,754 A | 3/1995 | Lambotte et al. | 435/607.4 |
| 5,418,136 A * | 5/1995 | Miller et al. | 435/5 |
| 5,425,983 A | 6/1995 | Propst et al. | |
| 5,450,752 A | 9/1995 | White et al. | 73/643 |
| 5,455,072 A | 10/1995 | Bension et al. | 427/255.7 |
| 5,455,081 A | 10/1995 | Okada et al. | 427/528 |
| 5,458,852 A | 10/1995 | Buechler | 422/58 |
| 5,459,078 A | 10/1995 | Kline et al. | 436/518 |
| 5,468,606 A | 11/1995 | Bogart et al. | |
| 5,541,057 A | 7/1996 | Bogart et al. | |
| 5,552,272 A | 9/1996 | Bogart et al. | |
| 5,624,537 A | 4/1997 | Turner et al. | |
| 5,637,353 A * | 6/1997 | Kimock et al. | 427/255.3 |
| 5,639,671 A | 6/1997 | Bogart et al. | 436/518 |
| 5,658,723 A * | 8/1997 | Oberhardt | 435/4 |
| 5,777,372 A | 7/1998 | Kobashi et al. | |
| 5,880,552 A * | 3/1999 | McGill et al. | 310/313 |
| 5,883,769 A | 3/1999 | Choi et al. | |
| 6,023,540 A * | 2/2000 | Walt et al. | 385/12 |
| 6,096,068 A * | 8/2000 | Dobak, III et al. | 607/105 |
| 6,197,494 B1 * | 3/2001 | Oberhardt | 435/4 |
| 6,849,462 B1 * | 2/2005 | Winkler et al. | 436/180 |

FOREIGN PATENT DOCUMENTS

| | | |
|---|---|---|
| EP | 0 395 300 | 10/1990 |
| EP | 0326100 | 9/1993 |
| JP | 61-33645 | 2/1986 |
| WO | WO 91/13998 | 9/1991 |
| WO | WO 92/16826 | 10/1992 |
| WO | WO 93/24828 | 12/1993 |
| WO | WO 94/14066 | 6/1994 |
| WO | WO 98/10288 | 3/1998 |

OTHER PUBLICATIONS

Goddard et al., Real-time Biomolecular Interaction analysis using the resonant mirror sensor., Analyst, vol. 119, 583-588, 1994.*

Iqbal et al., Developent of Porous Antireflective Films on Borosilicate Glases, *Journal of the American Ceramic Society* 66(4):302-307 (1983).

Minot, "Single-layer, gradient refractive index antireflection films effective from 0.35 to 2.5µ," *J. Opt. Soc. Am.* 66(6):515-519 (1976).

J. Calvin Giddings, "Unified Separation Science", John Wiley & Sons, 1991, pp. 62, 74, and 75.

Supplementary European Search Report for Application No. EP 97 91 1850.

* cited by examiner

FLOW-THROUGH OPTICAL ASSAY DEVICES PROVIDING LAMINAR FLOW OF FLUID SAMPLES, AND METHODS OF CONSTRUCTION THEREOF

This application is a continuation-in-part of U.S. Ser. No. 08/742,755 filed Oct. 31, 1996, now abandoned, which is hereby incorporated by reference herein, including all tables, figures, and claims.

BACKGROUND OF THE INVENTION

The present invention relates to methods and devices useful for analytical testing. Such testing includes, but is not limited to medical diagnosis and environmental testing.

The following is a discussion of relevant art, none of which is admitted to be prior art to the present invention.

A flow-through, or porous, assay device is described in U.S. Pat. No. 4,632,901 by Valkirs, et al. In this method an immunoassay is performed on a membrane or filter which is coated with an antibody and is capable of removing an analyte from a sample applied to the membrane. Visualization is based on the analyte dependent capture of a secondary reagent which will act on a substrate and produce a colored, particulate product which will non-specifically adhere to the membrane only where the secondary reagent is present. Numerous modifications to this basic design have been introduced including colored, and/or metallic particles (U.S. Pat. No. 4,775,636) attached to the secondary reagent for visualization, and the introduction of chromatographic rather than flow-through techniques (U.S. Pat. No. 5,232,835).

U.S. Pat. No. 5,200,312 describes a membrane assay system where a colored, insoluble product is used for the detection of an analyte. This product is formed by an enzyme interacting with a substrate that contains a reagent which when exposed to the enzyme produces a chromophore containing insoluble product producing a visible color change. U.S. Pat. No. 5,395,754 describes methods for producing control or calibration zones on a membrane surface for use in a biological assay.

Production of porous antireflective films have been described (66 *J. Opt. Soc. Am.* 515-519, 1976; 66 *J. Am. Ceramic Soc.* 302-307, 1983). The antireflective films have steep refractive index gradients for making broad band AR layers. The films are highly porous with the pores being disordered and interconnected. The pores capture air within the AR material being formed which help produce a refractive index gradient.

Mass transport, or mass transfer, is a well established phenomena. It can arise from the presence of a concentration gradient, temperature gradient, electrical field, gravity, etc. Mass transport in a solution is very sensitive to solution movement or flow or convection. Mass transport may also be influenced by the diffusion coefficient or charge of materials in the solution.

In a static diffusion limited reaction, a concentration gradient can be formed as the diffusion layer is depleted and the analyte concentration is reduced at the surface. Analyte from a higher concentration zone in the sample must diffuse to the surface for binding. Only sample near the surface will be bound. Replenishing analyte to the diffusion layer or barrier limits the binding reactions. Convective mass transport effects can serve to disrupt or modify the diffusion barrier.

Solution flow, mass transport, in a highly porous or interconnected surface is turbulent, producing plug or convection flow characteristic. However, in a channeled surface, the hydrodynamic mass transport creates laminar flow characteristics. Plug flow causes the solution to mix by convection and then advance along its path. This ensures that the diffusion barrier is minimized as sample flows laterally across the porous material. In an assay system, plug flow could increase the probability of non-specific adhesion of non-analyte material and subsequent visualization reagents. However, the convective flow will tend to increase the contact of analyte with available binding sites as the flow path is followed by fresh solution which repeatedly contacts the available binding sites.

Solutions which flow through or across channeled material are essentially static when in contact with a solid, uniform surface until a channel is encountered. Flow through that channel creates laminar flow. Thus, while a reaction is diffusion limited, material flow is influenced such that the diffusion barrier or layer is disrupted. The convection introduced by channels continuously forces new analyte to the surface eliminating the dead layer near the pore. While, also preventing the formation of a diffusion barrier which meets the static condition between the pores. Thus, the laminar flow continuously brings new bulk into the diffusion boundary. It is commonly believed that the plug flow system is more efficient in overcoming the diffusion limitation than the laminar flow system. Applicant has suprisingly discovered that for the optical assay devices of the present invention laminar flow is more effective than plug flow systems.

In a static solution/solid reaction, the diffusion barrier, after 20 seconds, is $\delta(t)=2.8\times10^{-3}$ cm ($\delta(t)=2(D_o t)^{-1/2}$). $D_o$ is assumed to be $1\times10^{-7}$ cm$^2$/sec for common biologicals. In a hydrodynamic mass transport case, the diffusion barrier is essentially independent of time and $\delta(o)=3.7\times10^{-4}$ cm ($\delta(o)=1.61 (D_o)^{1/3} (\omega v^{1/6})^{-1/2}$) Where $\omega$ is the angular frequency based on a solution moving across an assumed solid having an angular velocity of $\omega$ and v is a function of the solutions viscosity (kinematic viscosity). The value of v based on a solution moving across an assumed solid having an angular velocity of $\omega$ was assumed to be 0.01 cm$^2$ sec$^{-1}$ (water). Calculations are derived from Ficks Law.

SUMMARY OF THE INVENTION

The present invention features means to introduce mass transport by laminar flow of a sample potentially containing an analyte across and through the layers of an optical assay device.

Such devices (see FIG. 1) comprise a support (channel-containing or porous), an optically functional layer, an attachment layer and may or may not contain an analyte specific receptive layer. The optically functional layer can be provided on the support by a thin film coating process. This layer contains the active components required to produce signal upon analyte binding and is selected based on the desired final assay device and the method of analysis used to interpret the assay results. This layer comprises an optical base layer with or without an antireflective layer. When the optically functional layer includes an AR material, the final assay device allows for visual determination of the assay result. The optically functional layer is coated with an attachment layer. The attachment layer is included to provide a stable environment for the retention of an analyte specific receptive material or a means by which the analyte itself is retained. Analyte binding to the specific receptive material on the attachment layer is achieved by either physical or chemical adsorption due to a specific interaction between an analyte and the analyte specific surface. Alternatively, when the analyte binds non-specifically to the attachment layer, analyte is detected through the subsequent specific binding of an analyte specific binding reagent.

Figure 2A:

One such means for producing mass transport/laminar flow is by providing a channel containing solid support (see FIG. 2A). The channel containing solid support can inherently contain the channels or can be modified to introduce channels by the removal of discrete, but limited, areas from up to 15% of the solid support. The optically functional layer is applied to the channel-containing support in a manner which will maintain the channels. Together these layers promote laminar flow of the sample.

Figure 2B:

Another means to achieve laminar flow of a sample through or across the layers of an optical assay device is to provide a channel containing optically functional layer and an underlying porous support (see FIG. 2B). The porous support while open to fluid flow, does not offer the desired channel flow characteristics or optical properties. Thus, the channels are introduced into the optically functional layer by chemical, mechanical, photochemical, lithographic or other known means. One requirement of this design is that the optically functional layer be applied such that the optical properties (primarily refractive index) are based on those of the optical base layer, not a composite of the base layer and the porous support.

Figure 2C:
Figure 3:
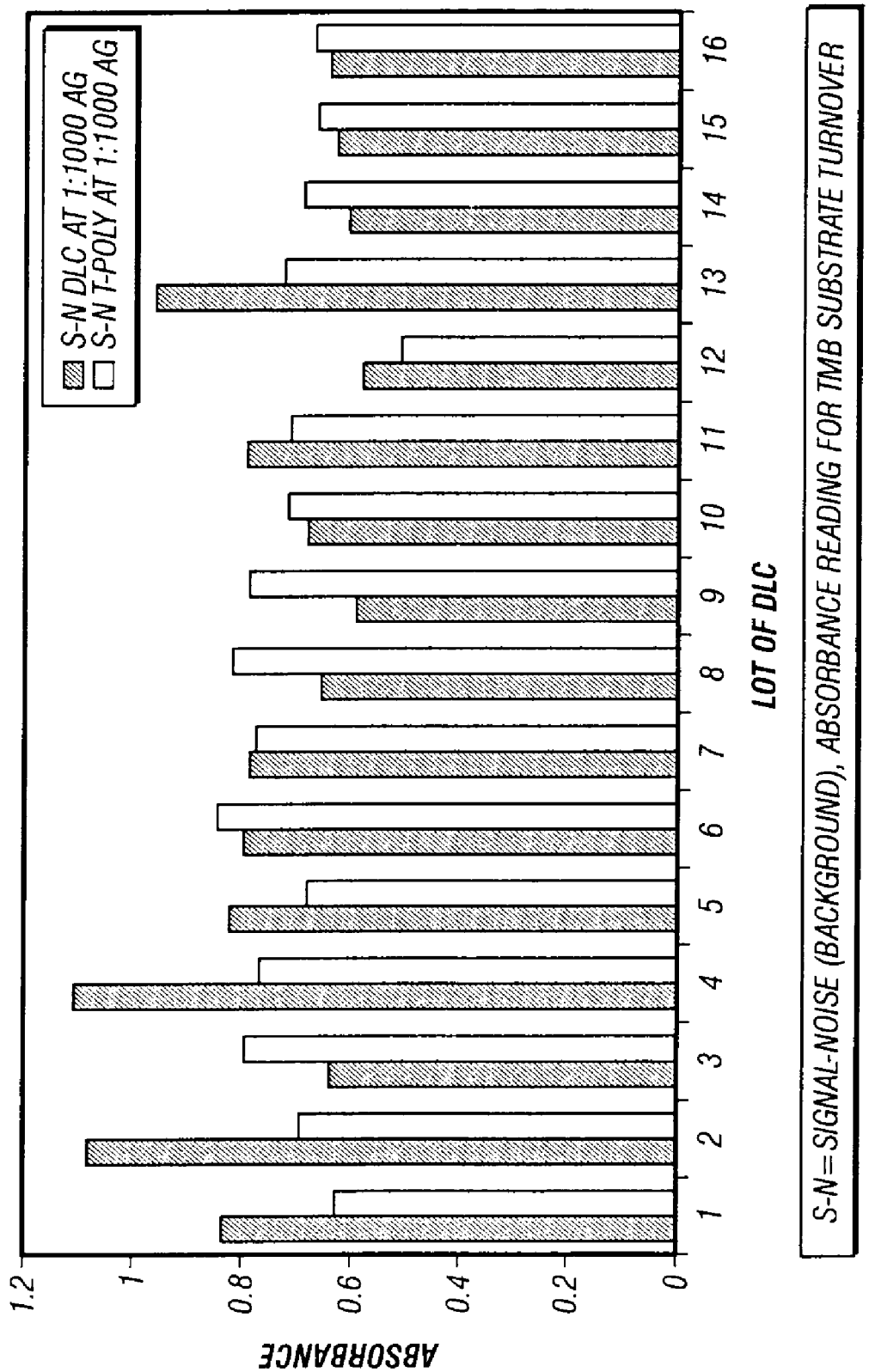
Figure 4:
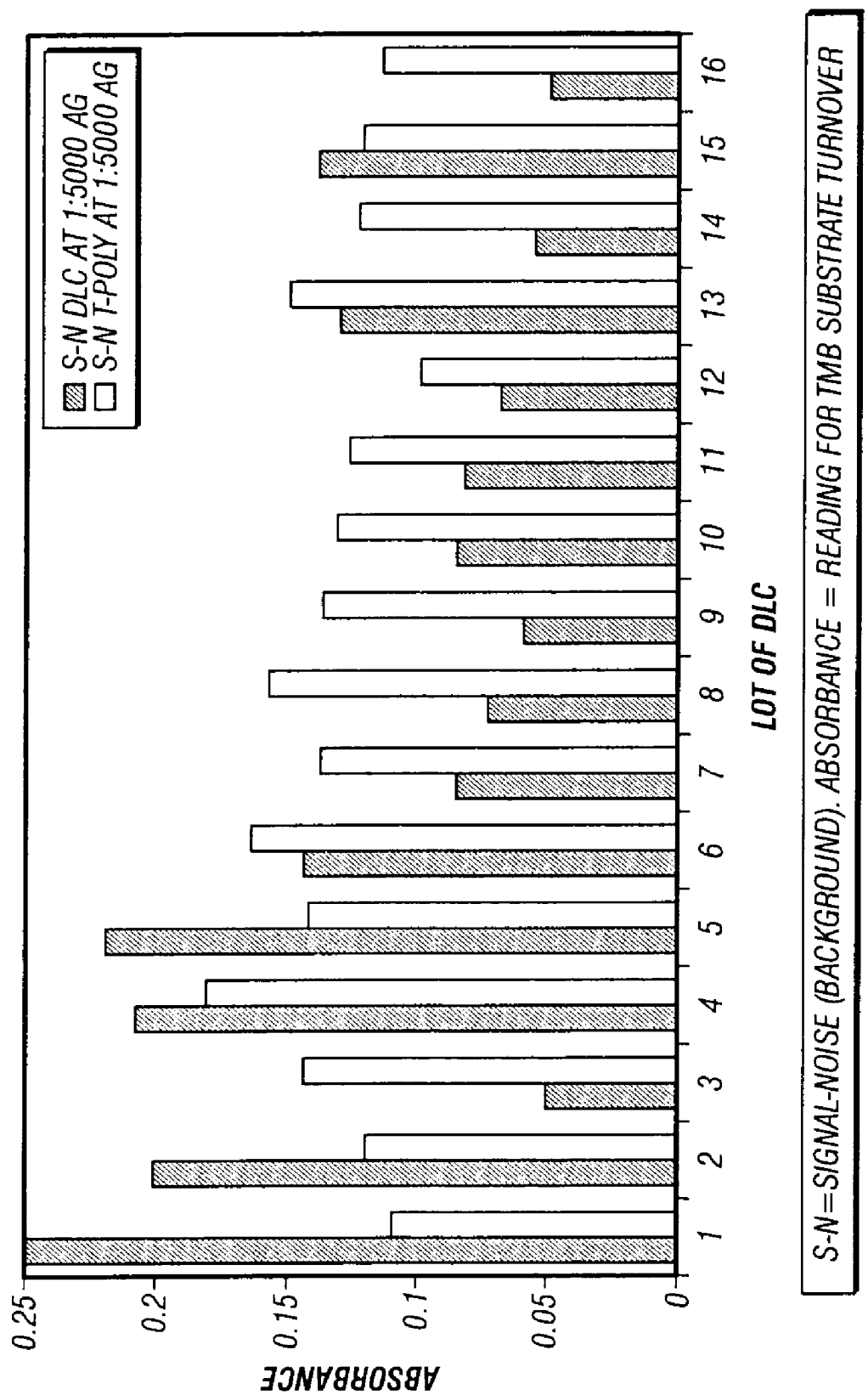

Alternatively, the optically functional layer can comprise discrete optically functional particles (spheres, rods, or fibers)(see FIG. 2C). These particles in conjunction with an underlying porous support provide channels which also result in the mass transport of the sample through or across the assay device by laminar flow. Careful control of the particle size and packing density is required to achieve the desired optical and flow properties. The solution below the optically functional surface containing solid particles may have plug flow with no affect on the binding and detection events.

The mass transport/laminar flow rate through and/or across the device can be modified by the use of absorbent material positioned around or underneath the layers of the assay device. Absorbent material allows for wicking which acts to draw fluid through or across the layers of the device. Also, although sample will flow through the device without external assistance, it may be pulled or pushed through the channels of the device (by negative or positive pressure respectively) either continuously (in-line sampling) or in a discrete volume.

Mass transport/laminar flow of sample through the device allows for an increased contact of the bulk sample with the surface of the optical device where binding of analyte occurs. It also modifies the diffusion barrier or disrupts the concentration gradient set-up at the diffusion barrier. This action causes the amount of available analyte exposed to the receptive layer (or attachment layer) of the device to be increased. The laminar flow of solution introduces more analyte to the receptive layer (or attachment layer) throughout the solution's total surface contact period. In a simple diffusion-limited reaction, once the diffusion layer is depleted, very little additional analyte is made available to the surface receptive material.

The layers of the present device which, when exposed to solution or gas, allow analyte to move to the surface through mass transport/laminar flow. Mass transport, to the surface will be governed by the number and distribution of channels, sample parameters, and laminar flow created on or within the layers of the device. Channels can be created by the use of perforation, etching or the agglomeration and or immobilization of particles on or in the surfaces. Applicant has discovered that the mass transport effect by laminar flow eliminated the diffusion limitation of a solid surface assay by reducing concentration gradients within the sample fluid, while maintaining the desired optical properties.

The channels present in the layers of the optical assay device to create a mass transport/laminar flow effect, do not significantly contributed an increased binding area for the analyte. Binding is confined to the surface of the device which contains an analyte specific binding layer. Electron microscopy suggests that no material binds near the channels. Furthermore, any binding events which could occur within the channels are transparent to the optical or mass detection methods employed. Any method that measures a change in thickness, mass, optical mass, or some other physical property of the thin film device after binding or reaction with the analyte is a suitable means for direct physical detection. Those methods can be automated, instrumented or simple, visual color determination. The channeled surfaces are not designed to retain any analyte or secondary reagent for the detection of analyte, but are only designed to increase the volume of sample made available to the analyte binding sites at the surface of the device.

In a first aspect, the invention features an optical assay device for the detection of an analyte of interest in a sample comprising a support containing channels, an optically functional layer positioned on the support such that the optically functional layer and the support allow for laminar flow of the sample through layers of the device, an attachment layer positioned on the optically functional layer, and an analyte specific receptive layer positioned on the attachment layer.

By "sample" is meant any fluid medium, gas or liquid. Samples may be used which are high in dissolved solids without further processing and samples containing high solids (non-dissolved) may be introduced through a filter or used in conjunction with additional manual steps. Samples may be a gas, a liquid, a suspension, extracted or dissolved sample, or a supercritical fluid. Some flow properties must exist in the sample or extract to allow for mass transport/laminar flow.

Analytes may be antigens, antibodies, receptors, ligands, chelates, proteins, enzymes, nucleic acids, DNA, RNA, pesticides, herbicides, inorganic or organic compounds or any material for which a specific binding reagent may be found. The surfaces can be used with multiple analytes and the designation of specific interaction can be made clear with the use of surface patterning to resolve differing analytes.

By "support containing channels" is meant that the support contains channels or holes. The support may have pre-existing channels (which inherently contain the desired diameter and density) or the channels may be created by the removal of material from the support (by any process, mechanical, photochemical, electrochemical, or chemical, which etches, drills, punctures, or in other manner introduces channels or holes into the support). Flow rate of the solution is influenced by a combination of channel size and channel density, in addition to certain sample characteristics, e.g., viscosity.

By "optically functional layer" is meant a layer which can produce a signal upon the binding of analyte to a receptive layer. The layer may have one or more coatings, including the base layer with or without an antireflective layer, designed to modify the optical properties of the support material so that the desired degree of reflectivity, transmittance, and/or absorbance is suited to the final assay configuration. The optically functional layer may attenuate one or more, or a range of wavelengths of light so that a result is observable visually or by instrumented analysis in the final device upon analyte binding. The attenuation of the light may involve extinction or enhancement of specific wavelengths of light as in an AR coated assay device for a visually observable color change. Or the intensity of a specific wavelength of light may be modified upon reflection or transmittance from the final assay device. The optically functional layer may also modify the optical parameters of the device to allow a change in the state or degree of polarization in the incident light.

By "laminar flow" is meant the process by which the diffusion layer near the surface of the optical assay device is reduced and the amount of analyte made available to or in contact with the receptive layer (or attachment layer) is increased. Laminar flow is smooth and steady and occurs as if separate layers (laminae) of the fluid have steady and characteristic velocities with net flow in one direction.

By "through layers of the device" is meant both flow of the sample through the layers from the surface of the device toward the support and flow across the surface of any layer of the device.

By "attachment layer" is meant any material or materials which promote or increase the binding of receptive material to the optically functional layer. Also, the attachment layer should retain the receptive material with sufficient avidity for all subsequent processing and assay processes. The attachment layer must not reduce the stability of the receptive material but may increase that stability. When no receptive layer is utilized, the attachment layer non-specifically binds the analyte.

By "analyte specific receptive layer" is meant a material or materials which have sufficient affinity to bind the analyte to allow for analyte detection and which is specific for the analyte of interest.

In a second aspect, the invention features an optical assay device for the detection of an analyte of interest in a sample comprising a support containing channels, an optically functional layer positioned on the support such that the optically functional layer and the support allow for laminar flow of the sample through layers of the device, and an attachment layer positioned on the optically functional layer.

In this aspect the attachment layer (without a receptive layer) must be capable of non-specific capture of the analyte. Examples of attachment layers include silanes, siloxanes, various polymers, Ni, and diamond-like carbon. The analyte is detected by using an analyte specific binding reagent.

In a third aspect, the invention features an optical assay device for the detection of an analyte of interest in a sample comprising a porous support, an optically functional layer comprising discrete, optically functional particles embedded in the support such that the optically functional layer and the support allow for laminar flow of the sample through layers of the device, an attachment layer positioned on the particles, and an analyte specific receptive layer positioned on the attachment layer.

By "porous support" is meant a material which presents a solution a very tortuous path for flow.

By "discrete optically functional particles" is meant any particle, sphere, rod, which is in the 10 μm to 1 mm size range and can be packed into a porous support creating a uniform, refractive index layer in a localized portion of the porous support.

By "embedded" is meant that particles are trapped within the matrix of the porous support.

In a fourth aspect, the invention features an optical assay device for the detection of an analyte of interest in a sample comprising a porous support, an optically functional layer comprising discrete, optically functional particles embedded in the support such that the optically functional layer and the support allow for laminar flow of the sample through layers of the device, and an attachment layer positioned on the particles.

In a fifth aspect, the invention features an optical assay device for the detection of an analyte of interest in a sample comprising a porous support, an optically functional layer containing channels positioned on the support such that the optically functional layer and the support allow for laminar flow of the sample through layers of the device, an attachment layer positioned on the optically functional layer, and an analyte specific receptive layer positioned on the attachment layer.

By "optically functional layer containing channels" is meant that the optically functional layer has channels of the appropriate diameter and density to allow for laminar flow of sample through layers of the device. Channels can be introduced by chemical, mechanical, photochemical, lithographic or other means know to those skilled in the art.

In a sixth aspect, the invention features an optical assay device for the detection of an analyte of interest in a sample comprising a porous support, an optically functional layer containing channels positioned on the support such that the optically functional layer and the support allow for laminar flow of the sample through layers of the device, and an attachment layer positioned on the optically functional layer.

In preferred embodiments the optically functional layer comprises an antireflective layer; the attachment layer is nickel; the device further comprises an absorbent material surrounding the optically functional layer or beneath the support; the support comprises polyester or polycarbonate, the optically functional layer comprises a layer of silicon nitride positioned on a layer of amorphous silicon and the attachment layer comprises nickel; the support comprises polycarbonate or polyester, the optically functional layer comprises a layer of diamond-like carbon which is positioned on a layer of germanium; the optically functional layer comprises a layer of diamond-like carbon which is positioned on a layer of germanium, and the attachment layer comprises nickel; the optically functional layer comprises a layer of silicon nitride positioned on a layer of amorphous silicon; the attachment layer comprises diamond-like carbon; analyte is selected from the group consisting of antigens, antibodies, receptors, ligands, chelates, proteins, enzymes, nucleic acids, DNA, RNA, pesticides, herbicides, inorganic or organic compounds.

Antireflective layers are known to those skilled in the art. Examples of some AR layers that are suitable for use in the present invention include aluminum oxide, antimony oxide, bismuth oxide, indium oxide, indium tin oxide, tin oxide, silicon monoxide, titanium dioxide, zirconium oxide, silicon nitride, silicon oxynitride, germanium oxides, cobalt oxides, carbon, tantalum oxide as well as most other metal oxides, carbides, nitrides or oxy-nitrides, diamond and diamond-like carbon.

By "absorbent material" is meant a material which has a capacity to draw (wick) and retain solution away from a surface that the material is in contact with. The material can surround the optically functional layer and/or be positioned under the support. Use of a combination of material of increasing or decreasing absorbance allows for control of sample movement.

A further preferred embodiment is the use of polycarbonate as the support, germanium as the base optical layer (>300 Å), and diamond-like carbon which functions as both the antireflective and the attachment layers (300-800 Å depending on the color change selected or desired).

In a seventh aspect, the invention features a method for detecting the presence or amount of an analyte in a sample comprising the steps of providing a device comprising a support, an optically functional layer positioned on the support, an attachment layer positioned on the optically functional layer, an analyte specific receptive layer positioned on the attachment layer, applying a sample to the device such that the sample is drawn by laminar flow through or across layers of the device, and the analyte binds to the analyte receptive layer causing a mass change on surface of the device thus indicating the presence or amount of the analyte in the sample.

By "through and across all layers" is meant that sample solution will flow vertical and/or horizontal to or through the optical device depending on the device design and channel distribution.

By "mass change" is meant a change in thickness, optical thickness (refractive index×thickness), or material deposition (mass or optical mass) on the optically functional layer. Mass change can be an increase or decrease in one or more of the surface materials.

In an eighth aspect, the invention features a method for detecting the presence or amount of an analyte in a sample comprising the steps of providing a device comprising, a support, an optically functional layer positioned on the support, an attachment layer positioned on the optically functional layer, and applying the sample to the surface of the device such that the sample is drawn by laminar flow through or across layers of the device, the analyte binds to the analyte attachment layer, and providing an analyte specific binding reagent which binds the analyte bound to the attachment layer causing a mass change on the surface of the device thus indicating the presence or amount of the analyte in the sample.

By "analyte specific binding reagent" is meant a reagent which will specifically react with the surface captured analyte.

In preferred embodiments the support contains channels; the support is porous and the optically functional layer comprises particles; the support is porous and the optically functional layer contains channels.

In a ninth aspect, the invention features a method for constructing an optical assay device with laminar flow properties, comprising the steps of providing a support, providing an optically functional layer on the support such that the optically functional layer and the support allow for laminar flow of a sample through or across layers of the device, providing an attachment layer on the optically functional layer, and providing an analyte specific receptive layer on the attachment layer.

The optically functional layer may participate in the laminar flow by conforming to channels present in the underlying support, or by having channels or holes directly introduced into the optically functional layer which direct sample down to a porous support, or by comprising particles which create channels or holes through which sample passes down to a porous support.

In a tenth aspect, the invention features a method for constructing an optical assay device with laminar flow properties, comprising the steps of providing a support, providing an optically functional layer on the support such that the optically functional layer and the support allow for laminar flow of a sample through or across layers of the device, and providing an attachment layer on the optically functional layer.

In preferred embodiments, the support contains channels; the support is porous and the optically functional layer comprises particles; the support is porous and the optically functional layer contains channels.

In an eleventh aspect, the invention features a composition comprising a support and an optically functional layer which is useful for promoting laminar flow of sample through the layers.

By "promoting laminar flow of sample" is meant a material or design or process which causes sample solution to move through or across the optical assay device under conditions which establish a mass transport/laminar flow.

In a preferred embodiments, the support contains channels; the support is porous and the optically functional layer comprises optically functional particles; the support is porous and the optically functional layer contains channels; the support comprises polycarbonate and the optically functional layer comprises a layer of amorphous silicon; the support comprises polycarbonate and the optically functional layer comprises a layer of silicon nitride positioned on the amorphous silicon; the support comprises polycarbonate and the optically functional layer comprises germanium; the support comprises polycarbonate and the optically functional layer comprises a layer of diamond-like carbon positioned on a layer of germanium; the support comprises polyester and the optically functional layer comprises amorphous silicon; the support comprises polyester and the optically functional layer comprises a layer of silicon nitride positioned on a layer of amorphous silicon; the support comprises polyester and the optically functional layer comprises germanium; the support comprises polyester and the optically functional layer comprises a layer of diamond-like carbon positioned on a layer of germanium.

In a twelfth aspect, the invention features a composition of diamond-like carbon useful as an attachment layer.

In a thirteenth aspect, the invention features an assay device for the detection of an analyte of interest comprising a support, and an attachment layer positioned on the support comprising diamond-like carbon.

In a fourteenth aspect, the invention features an optical assay device for the detection of an analyte of interest comprising a support, an optically functional layer positioned on the support, and an attachment layer positioned on the optically functional layer comprising diamond-like carbon.

By "assay device" is meant a device useful for the detection of an analyte.

By "support" is meant any surface on which an assay for an analyte can be performed including but not limited to microtiter plate, ceramics, metals, slides, cuvettes, test tubes, diffraction gratings for surface plasmon resonance, membranes, filter paper, silicon, glass, piezoelectric structures for resonance or oscillation studies, and any compatible surface/detection system combinations. Coatings can be applied uniformly over the surface of the support or in unmasked areas of the support. Supports may be in a range of shapes and configurations.

By "attachment layer" is meant any material or materials which promote or increase the binding of the receptive material to either the support or the optically functional layer, if it is present in the device. When no receptive layer is utilized, the attachment layer non-specifically binds the analyte.

By "diamond-like carbon" is meant a layer composed of a uniform film or packed particles which consist of diamond (synthetic or natural), monocrystalline diamond, resin type diamond, polycrystalline diamond, diamond-like carbon, amorphous carbon with diamond like properties (hardness and surface energy), amorphous hydrogenated DLC or carbon films, non-crystalline to crystalline carbon films with diamond like properties or diamond-like material with a chemical composition ranging from graphite-like to diamond.

By "optically functional layer" is meant a layer which can produce a signal upon the binding of analyte to a receptive layer or which can produce a signal upon binding of analyte non-specifically to an attachment layer along with binding of an analyte specific reagent. The layer may have one or more coatings, with or without an antireflective layer, designed to modify the optical properties of the support material so that the desired degree of reflectivity, transmittance, and/or absorbance is suited to the final assay configuration. The optically functional layer may attenuate one or more, or a range of wavelengths of light so that a result is observable visually or by instrumented analysis in the final device upon analyte binding. The attenuation of the light may involve extinction or enhancement of specific wavelengths of light as in an AR coated assay device for a visually observable color change. Or the intensity of a specific wavelength of light may be modified upon reflection or transmittance from the final assay device. The optically functional layer may also modify the optical parameters of the device to allow a change in the state or degree of polarization in the incident light.

In preferred embodiments of these devices, an analyte specific receptive layer is positioned on the attachment layer; the attachment layer non-specifically binds analyte selected from the group consisting of antigens, antibodies, receptors, nucleic acids, polysaccharides, lipopolysaccharides, enzymes, proteins, microorganisms, fragments derived from microorganisms, haptens, drugs, food contaminants, environmental agents such as, but not limited, to dioxane, and allergens, ligands, chelators, and analogs or derivatives thereof; the receptive layer comprises biomolecules selected from the group consisting of antigens, antibodies, receptors, nucleic acids, polysaccharides, lipopolysaccharides, enzymes, proteins, microorganisms, fragments derived from microorganisms, haptens, drugs, food contaminants, environmental agents such as, but not limited to, dioxane, and allergens, ligands, chelators, and analogs or derivatives thereof; the diamond-like carbon is coated on the support to a thickness of 50 Å; the diamond-like carbon is coated on the optically functional layer to a thickness of 50 Å; the diamond-like carbon is coated on the support to a thickness of 50 to 3000 Å; the diamond-like carbon is coated on the optically functional layer to a thickness of 50 to 3000 Å; the diamond-like carbon is coated on the support by a process selected from the group consisting of shock-synthesis technique, sputtering, thermal radio-frequency and microwave-supported plasmas, heated filament, direct current plasma, ion beam technique, chemical vapor deposition, plasma deposition, and ion beam gun; the diamond-like carbon is coated on the optically functional layer by a process selected from the group consisting of shock-synthesis technique, sputtering, thermal radio-frequency and microwave-supported plasmas, heated filament, direct current plasma, ion beam technique, chemical vapor deposition, plasma deposition, and ion beam gun; the diamond-like carbon comprises industrial diamonds.

Processes for coating diamond-like carbon are described in Bachmann et al., *Chemical and Engineering News*, page 24, May 15, 1989.

By "biomolecule" is meant material which is an analyte of interest or which specifically binds an analyte of interest (i.e., a receptive layer) Biomolecules include antigens, antibodies, receptors, nucleic acids, polysaccharides, lipopolysaccharides, enzymes, proteins, microorganisms, fragments derived from microorganisms, haptens, drugs, food contaminants, environmental agents such as, but not limited to, dioxane, and allergens, ligands, chelators, and analogs or derivatives thereof.

One advantage of the present invention is an enhanced sensitivity due to an increase in the available or useable sample volume which is brought in contact with the analyte specific receptive material by the mass transport/laminar flow effect. This system can provide an increase in analytical sensitivity of at least 40 fold.

A second advantage is the reduction of the assay performance time. The incubation times are decreased by delivering new analyte to the surface through fluid mass transport/laminar flow which does not occur in simple diffusion. The time per step basis is reduced from the minute time scale to the seconds time scale due to efficient delivery of material to the surface by mass transport/laminar flow and increasing the sample volume applied to the surface. The increased sensitivity and speed will be especially useful for the detection of analytes such as antigens or DNA in samples.

A third advantage is that the incubation time can be controlled by the wicking rate, differential pressure, channel size, and sample viscosity, rather than manually timing each step. All subsequent surface incubation times may be of a similar time frame. Another possibility is to use layers of wicking materials with different capillary rates, wetability rates, or flow characteristics to control incubation times.

A fourth advantage is ease of manufacturing. The materials which are useful as layers of the devices are compatible with continuous on line web processing. All optical processing can be done in one step or one continuous operation. There is also an economy of scale as large sheets of materials can be processed. In addition, the yield for any one step is improved over that of manufacturing discrete components of a device. Furthermore, attachment layers (e.g., Ni, diamond-like carbon) can be applied while processing the optical layers. Also, use of these materials allows for flexible optical design, as the optical layers can be readily interchanged and additional layers of materials (e.g., AR, receptive layer) can be easily added.

A fifth, the advantage of using a device which utilizes mass transport/laminar flow characteristics in an automated system is that samples may flow through the surface eliminating the need for vacuum and pressure rinsing which creates aerosols and makes containment difficult.

The methods and devices of the present invention are distinct from the prior analytical methods which all rely on the adhesion or capture of an analyte specific reagent within the numerous pores or fibers within the membrane or filter material. In these methods, such membrane or filter material is used to contain the specific binding reagent, separate the unreacted sample material from the bound analyte and increase the surface area available for binding reagent. The binding reagent is found on the surface and within the pores and detection can occur to some depth within the porous material dependent on the signal generation method used. These materials employ overall porosities of 60%. The pore sizes of these materials are on the order of 0.45 microns. The pores or networked surfaces are highly complex and interconnected. This introduces a plug flow type of system. In distinction, in the present invention the channels do not exceed 15% of the total surface area of any layer and are discrete with no interconnections producing a flow that is laminar in character. A further distinction is that binding of analyte within the pores or channels is insignificant and does not contribute to the generation of detectable signal.

Pores have been introduced into an antireflective layer to alter the optical properties of that layer and create a gradient in the refractive index. In contrast, in the present invention channels are introduced into the optically functional layer only to allow for the laminar flow of sample through an assay device. Furthermore, very disordered highly porous films used to produce broadband AR films are not compatible with the desired devices of this invention. In a biological assay, these types of porous AR films would tend to encourage the majority of binding events to occur within the porous film not at the surface of the AR film. Also, broadband AR films produce very weak and minor color change with a corresponding change in thickness or mass. The devices of the current invention use narrowband AR layers which are designed to produce very strong color changes which are extremely intense. Color transitions occur over a very small thickness range.

The materials and methods described in this application can be used across a wide range of analytical testing needs. In particular, the devices produced with these processes are of utility to the medical diagnostic field. The devices may be used in a wide range of applications where analyte capture is required, including but not limited to: infectious disease testing, cancer diagnosis, drug monitoring, environmental testing, therapeutic drug monitoring, DNA testing, and cardiac testing. The devices produced with these materials and methods can be used in fields as diverse as medical diagnostics and environmental monitoring or food screening and testing applications.

Other features and advantages of the invention will be apparent from the following description of the preferred embodiments thereof, and from the claims.

The articles and publications in this application are hereby incorporated by reference.

DESCRIPTION OF THE PREFERRED EMBODIMENTS

The drawings will briefly be described.

DRAWINGS

FIG. 1 is a schematic diagram of the layers of a channel-containing optical device. All layers illustrated need not be included in any particular embodiment of such a device. The location of channels is not shown.

FIGS. 2A-C are schematic diagrams of the possible combinations of support and optically functional layers that allow for laminar flow of sample through the device. FIG. 2A shows a device in which the flow characteristics desired in the final assay device are introduced through the support material which contains channels. FIG. 2B shows an optically functional layer with channels on a porous support. FIG. 2C shows a combination where a porous support is selected and the channels are created by packing of discrete particles which also impart the optical functionality to the final device.

FIG. 3 is a graph comparing diamond-like carbon (DLC) to T-Polymer for capture of Chlamydia specific lipopolysaccharide (LPS) at 1:1000 dilution of LPS. The y-axis indicates the absorbance reading for TMB substrate conversion to product corrected for background (absence of LPS). The lot of DLC is represented on the x-axis. Solid rectangles represent T-polymer. Stippled rectangles represent DLC.

FIG. 4 is a graph comparing diamond-like carbon (DLC) to T-Polymer for capture of Chlamydia specific lipopolysaccharide (LPS) 1:5000 dilution of LPS. The y-axis indicates the absorbance reading for TMB substrate conversion to product corrected for background (absence of LPS). The lot of DLC is represented on the x-axis. Solid rectangles represent T-polymer. Stippled rectangles represent DLC.

SUPPORT

A range of materials are suitable for the production of the channel containing support. They include cellulose acetate, PETE, polyesters, polycarbonates, glass particles, silica particles, $TiO_2$ particles, metal and non-metal particles, woven and non-woven materials, nylon, filter paper, membranes, polysulfones, porous glass, polypropylenes, polyurethanes or any polymer, plastic, and metals or non-metals. The support should provide the very limited distribution and size of channels (in flow across or over surface arrangements) required to allow mass transport/laminar flow in the final device.

The channels must be 0.01 to 14 microns and must not exceed 15% of the total surface area. Channel distribution should be relatively uniform across the surface. The channel may be an inherent property of the selected support or may be introduced into the support. The support may be chemically, photochemically, mechanically, or electrochemically modified. For example, two dimensional microporous screens can be created by bombardment of a polyester or polycarbonate web material between fusion plates and subsequent etching in a hot base bath for a period of time required to etch away the desired channel diameter. The support may be between 10 μm to 30 μm in thickness. The advantage of a limited channel density is the production of non-tortuous paths which permit for low outgassing in the subsequent deposition steps, and reduction of material retained in the channel structure. The channels created are discrete and there is no interconnection within the materials.

There are no limits on the support as long as the base optical layer can be applied to all surfaces uniformally (the base optical layer must remain intact for the optical detection of analyte) and it does not interfere with mass transport/laminar flow of the sample solutions applied to the uppermost surface of the final optical device.

No specific optical qualities need be inherent in the support. However, with thinner base optical layers deposited on the support, a light absorbing support provides an optical stack that is easier to visualize with the unaided eye, due to absorption of stray light and the removal of light passing from the back surface to the front.

The support should be chemically inert to the solvents involved in extraction or carrier solvents of the analyte of interest. For example, preferred inexpensive robust supports include polyester and polycarbonate which are unaffected by the solutions used in performing current applications.

The channels of the solid support can be controlled such that the use of wicking or fibrous underlying materials are not necessary to facilitate flow through or over the device. However, very controlled flow can be obtained by matching the channels of the support and a fibrous backing such that the average resident time for the sample volume remains within a specific time window. Control of flow through or over the device is only to assure that the reaction times remain constant within a given set of time parameters. An absorbent pad at one end or underneath the support may be required for solution containment and to assure that flow rates dictated by the wicking material remain constant with saturating volumes of solution. When differential pressures control flow rates the absorbent will be placed for solution uptake and containment purposes.

When the support is a highly porous, tortuous path material, the base optical and AR layers may be used to control the channeled effect. Highly porous materials may not be compatible with the optical devices of this invention. These supports could introduce scatter or other undesirable effects. The base optical layer over this porous support should be thick enough to cause the refractive index of the bulk base material to predominate in the device design.

Optically Functional Layer

The optically functional layer consists of a base layer and may also consist of an AR layer.

The base optical layer serves to provide the optical characteristics required for creating the appropriate reflectance, AR, adsorption, or transmission properties. It must be sufficiently dense to eliminate stray light leaking or back scattering from the backside of the support. The material must have a refractive index of greater than 3.0, so that it controls the gross percent reflectivity. This will impact AR layer selection by value of the refractive index and suitability to the instrumented formats, by controlling reflectivity or transmittance etc. If the base layer is too thin then the effective refractive index may be based on the composite indices of the base optical layer and the support. A wide range of thicknesses are possible for the base layer once the above limitations are addressed.

Thicker layers of base optical material will increase the percent reflectance. Lower reflectivities are important in visualizing the color change with the unaided eye. However, in an automated system higher reflectivities are important to sensitize small thickness changes for instrumental analysis.

Any base optical material may be used for production of the new device. Various films deposited on the channel containing solid support surface, or the spheres, rods, or fibers embedded in the porous supports may consist of but are not limited to amorphous silicon, polycrystalline silicon, lead telluride, titanium, germanium, cobalt, gallium, tellurium, iron oxide, or chromium. It has been found that alteration of the thickness of the base optical film on the support can be used to control overall reflectivity of the optical surface which will have applications in the use of automated systems and in tailoring the optical surfaces for various devices. But this has no significant impact on the color change assay methods.

The base optical layer may conform to the channels in the support or channels may be directly introduced into the base optical layer or particles may be used which do not require an underlying channel-containing support.

Over the base optical material can be applied one or more antireflective (AR) layers. These layers may consist of: aluminum oxide, antimony oxide, bismuth oxide, indium oxide, indium tin oxide, tin oxide, silicon monoxide, titanium dioxide, zirconium oxide, silicon nitride, silicon oxynitride, germanium oxides, cobalt oxides, carbon, tantalum oxide as well as most other metal oxides, carbides, nitrides or oxy-nitrides, diamond and diamond-like carbon. All AR materials may be applied by processes known to those skilled in the art.

For a visual assay device, the device must support a base optical layer with a higher index than the AR layer to be formed on the side opposite of the base layer. The preferred embodiment is in the use of a base optical layer that has a real refractive index that approximates the square of the real index of the AR layer. The imaginary index of the base optical layer need not fit any specific function.

The AR layer must have a real refractive index which approximates the square root of the real index of the base optical layer. In addition, the imaginary index of the AR layer should be fairly low in order to minimize absorption of light by this layer. However, the absorption characteristics of the AR layer can be used to enhance wavelength dependence for use in automated detection systems, such as reflectance or scatter measurements or detection of extinction parameters. The number of AR layers can be from one to four before the optical characteristics begin to break down. However, fewer numbers of layers offer advantages in ease of development and manufacture.

The compatibility between layers need only be that they adhere well enough to each other for the test result to be visualized and permanent if possible. Higher index compatible materials throughout the stack offer the advantage of higher contrast color changes for smaller thickness changes of the analyte specific layers.

The preferred color change will be from a gold or yellow to blue color upon attachment of the specific analyte to the surface. The thickness of analyte film needed to promote such a color change and the color density of the color development can be controlled by the materials in the stack.

In depositing the AR layers on a channeled material, the AR material should not fill up channels with material so that they become plugged. Thicknesses can be controlled to eliminate significant plugging. Another reason for using a channeled-containing support such as polyester or polycarbonate is that the non-tortuous pathways will not tend to plug up as would tortuous pathway materials.

In the case of the use of an instrument designed to measure reflectivity, the AR layer can be adjusted such that the sharpest change in reflectivity occurs at a specific wavelength of interest upon interaction of the analyte specific surface with the analyte of choice.

In the case of the visual test, the thickness of the layers can be set such that a thickness change will provide a sensitive color development. The AR layers used are deposited such that a gold to blue color change defined as sensitive color change because it constitutes the highest contrast color change (to the human eye) in antireflection conditions. Other color combinations may provide easier interpretation or flexibility to the assay format. All are easily obtained by changing material combinations and/or thicknesses.

A laminar flow effect can also be achieved by deposition of small particles coated with an AR layer and a biological binding layer (receptive material) then implanting these within a porous support. The AR coated particles may also be used in the chromatographic format, may be easily patterned, and maintain the permeability of the support. The AR coated beads must be packed into the membrane to provide sufficient density and uniformity in refractive index to prevent loss of signal due to scattering or absorption of incident light. Particles should be in the 1 µm to 3 µm size range and pack well into the porous support to provide a dense uniform optical surface.

The particles aid to promote mass transport/laminar flow of fluid media to the surface of the optical device by allowing flow around the particles into the porous or adsorptive support. In addition, the use of particles offers the flexibility of a chromatographic format wherein the analyte binds and fluid moves the particles through a tortuous or non-tortuous path to an immobilization or concentration area for detection.

Attachment Layer

A large number of chemical modifications of the optically functional layer can be made by silanes, siloxanes, and various polymers. These may be deposited in the vapor phase, sprayed, or dipped. Solution chemistry may be used to introduce additional materials to the surface. These materials are used to promote and enhance adhesion or attachment of the analyte specific binding reagent to the optically functional layer or provide a surface for non-specific capture of an analyte. In the case of non-specific capture, specific identification of the analyte is achieved with an analyte specific reagent which binds captured analyte. When the surface modifier latexes are used to bind the analyte specific binding layer, they produce a minor contribution to the total optical surface but are considered relevant to the design of the total device. Thus, one layer, preferably the AR layer, is adjusted to compensate for the added material.

The thickness of the attachment layer will be optimized for each specific capture molecule or analyte. The attachment layer will not have an appreciable affect on the channels. The attachment layer thickness will be less than 10 times as thick as the AR layer. The metals may also help stabilize molecules which are weakly bound to the AR layer.

While the attachment layer itself does not play a significant role in the optical characteristics of the stack. The attachment layer too can be altered to fit a visual or instrumented format. In the instrumented format, the attachment layer morphology may be controlled in order to fine-tune the reflectance characteristics required for the best sensitivity and selectivity. In altering the morphology the absorbance characteristics of the thin film can be controlled.

The attachment layer must bind protein or undergo some thickness change itself upon analyte capture. The attachment layer need not fit any particular physical characteristics as the thickness and conditions of this layer offer much flexibility to the stack design. A range of materials are well suited as attachment layers. These include the chemical modifiers such as silanes, siloxanes or polymers. In addition, a diamond-like carbon can serve as a hydrophobic attachment layer.

Surprisingly, an inorganic attachment layer for the analyte specific reagent has been found to work well in these optical assay devices. Materials which function in this role include platinum, nickel, gold, nichrome (80% nickel, 20% chromium), and bismuth oxide overlaid with gold where the bismuth oxide is included to promote the adhesion of the gold layer. These materials may be deposited via a vacuum vapor deposition, sputtering, photoreduction, or electrochemical reduction of a metal at the surface if semiconductor or conductive materials are used as the AR layer. Examples of semiconductor materials include titanium dioxide and silicon nitride. While representative conductor materials are indium tin oxide (ITO) or tin oxide. The preferred embodiment is the use of vacuum deposition technology to apply the metal layer. The advantage of vacuum vapor deposition is that it allows for tighter control of the deposited thickness and rapid processing of web materials. The thickness range can be from subnanometer to 5 nanometers without greatly affecting the AR layer or reflections. Greater than 5 nm can be coated with nickel, nichrome, and platinum if the underlying AR layer is at the thinner edge of its optimal thickness range without appreciably affecting the AR condition. However, the thicker metal layers decrease the reflected intensity due to absorption and therefore, should be kept as thin as possible while promoting increased adhesion of biomolecules. The layer should be between 10-100 Å. In addition, annealing and other treatments can be used to change the morphology of the inorganic attachment layers.

A preferred attachment of specific capture molecules will be based on interaction of the molecules with a nickel layer on the surface of the AR coating. The nickel layer will be between 1 and 10 nm thick. Deposition of the nickel layer will preferably be done by vacuum vapor deposition. Vacuum vapor deposition will allow for very tight control over the thickness and excellent repeatability from lot to lot.

Films consisting of diamond or Diamond Like Carbon (DLC), a coating which maintains many properties of diamond and some of graphite, are well known. DLC is used to describe a layer composed of a uniform film or packed particles which consist of diamond (synthetic or natural), monocrystalline diamond, resin type diamond, polycrystalline diamond, diamond-like carbon, amorphous carbon with diamond like properties (hardness and surface energy), amorphous hydrogenated DLC or carbon films, non-crystalline to crystalline carbon films with diamond like properties or diamond-like material with a chemical composition ranging from graphite-like to diamond. DLC is extremely hard, chemically resistant (inert), optically transparent, and has the thermal and low friction characteristics of pure diamond coatings. DLC films can range in hardness and composition from amorphous carbon to semicrystalline diamond like carbon to single crystal diamond. DLC film can be generated on supports by techniques such as chemical vapor deposition, sputtering, and ion beam deposition methods, plasma deposition, ion beam gun, thermal radio-frequency or microwave-supported plasmas, heated filament, direct current plasma and shock-synthesis techniques.

Graphite consists of ring structures formed from $sp^2$ hybridized carbon atoms. Diamond consists of covalently bonded aliphatic $sp^3$ hybridized carbon atoms. DLC depending on the deposition method will have varying amounts of $sp^2$ and $sp^3$ characteristics. Some of the DLC bonds may be terminated in hydrogen. The relative amount of the $sp^2$ and $sp^3$ character determines the overall film properties. Characterization of the film can be conducted by contact angle measurements (measures hydrophobicity), electron energy loss spectroscopy (EELS), reflection high energy electron diffraction (RHEED), and fourier transform infrared spectroscopy (FTIR). Carbon with $sp^3$ hybridization has a Raman peak at 1332 $cm^{-1}$ while carbon with $sp^2$ hybridization has peaks at 1345 $cm^1$ and 1540 $cm^{-1}$. A material that is a mixture of the two forms of carbon may exhibit a combination of these Raman peaks. The amount of $sp^2$ and $sp^3$ character also determines the film hardness. Varying the amount of hydrogen in the gas can affect the electron density, hardness, and other properties of the film including the hydrophobicity of the film.

As those skilled in the DLC coating art will appreciate, DLC can be coated onto a variety of support materials such as silicon, silicon coated supports, plastics, plastic silicon composites, ceramics, metals, or composites made from a combination of these materials. DLC can be made under low temperature (100° C. or less) or high temperature conditions. The DLC can be made from methane, olefinic gases, carbon monoxide, in the presence or absence of hydrogen. The deposition process from the carbon-containing gases can produce a variety of DLC films depending on the process type, temperature, gas composition, amount of non-carbon material, and other reaction conditions.

It has been discovered that DLC films on silicon or polycarbonate or other surface can strongly adhere biological molecules (biomolecules) such as antibodies, antigens, polysacchrides, lipopolysacchrides, nucleic acids, and other materials. While DLC coatings have been produced through a number of methods (all of which are suitable for the present invention), direct deposition through the use of ion beam techniques is the preferred method for providing hydrogenated DLC films for use as biological attachment coatings. Films can be produced at or near RT allowing for the use of a variety of substrate materials as previously described.

DLC coatings can be made by passing methane through an inductively coupled Rf ion gun whereby the methane is broken down to provide a hydrogenated amorphous diamond film. The process parameters and materials will determine the surface characteristics of the coated surface.

In addition to altering the hydrogen content of DLC (hydrogenated DLC), the hydrophobicity of DLC can be changed by altering the $sp^2/sp^3$ characteristics.

The DLC films used for the purposes of bioattachment typically range in hardness from 15-50 Gpa as measured by a nanoindenter. The refractive index of these films typically range from 1.5 to 2.2 as measure by a Gaertner ellipsometer. Biomolecule attachment appears to be equivalent over this range of material hardness and index. Although, not bound by any theory, it is generally believed that the lower hardness amorphous hydrogenated carbon films exhibit more hydrophobic character while the higher hardness films exhibit more electron rich sites due to the occurrence of more $sp^2$ character (C=C) on the surface.

The hydrophobic character is believed to be the primary mechanism for the attachment of biomolecules. However, the electron rich areas may promote electrostatic interactions as well. It is possible to tailor the hydrophobicity and electron density of the DLC surface to the type of biological molecule to be immobilized. This can be done based on an analysis of the $sp^2/sp^3$ characteristics of the surface and the characteristics of the biomolecule. For example, the more the $sp^3$ character of the DLC surface, the greater the hydrophobicity and the more the $sp^2$ character the greater the electron density (electrostatic surface). Those in the art are familiar with techniques to determine the hydrophobicity and electron density of biomolecules.

Alternatively, the surface/biomolecule can be matched for optimum retention of the biomolecule empirically. To empirically match a DLC surface and a biomolecule, a variety of DLC surfaces are produced. If the molecule is hydrophobic then the DLC is coated to supply surfaces of varying degrees of hydrophobicity. Techniques are known by those of skill in the art for varying parameters such as the deposition process, temperature, coating time, type and amount of carbon containing gas, presence, absence, or amount of non-carbon gas, and overall chamber pressure so that DLC surfaces can be produced which are varied in their hydrophobic character. The biomolecule is coated to the various test DLC surfaces from a coating solution of the same composition, ionic strength, pH, and amount of biomolecule. The coating of all surfaces is allowed to proceed at the same temperature for the same period of time. Surfaces are then washed and dried. The amount of biomolecule retained to the varying surface composition is determined. If an anti-biomolecule antibody is available it can be conjugated to horseradish peroxidase (HRP) for evaluation of the surfaces. A specific volume of a dilution of the anti-biomolecule antibody conjugate is applied to each of the test DLC surfaces for a period of time followed by a wash and dry step. Then a soluble TMB substrate solution is applied to the test DLC surfaces and incubated for a period of time. A specific volume of the solution is removed to microtiter wells containing a a pre-set amount of stop solution and the absorbance is measured. The absorbance measured correlates with the ability of the DLC surface to retain the biomolecule.

Alternatively, biomolecule binding can be monitored by measuring the contact angle of the surface. Thus, the change in contact angle (before and after biomolecule coating) may serve as an assessment of the amount of biomolecule retained. Other surface analysis techniques such as EELS, FTIR, RHEED can also serve to assess the retention of the biomolecule on the DLC surface.

A similar approach is used to assess DLC surfaces of varying electron density for the electrostatic retention of biomolecule. Techniques are known by those of skill in the art for varying parameters such as the deposition process, temperature, coating time, type and amount of carbon containing gas, presence, absence, or amount of non-carbon gas, and overall chamber pressure so that DLC surfaces can be produced which are varied in their electron density.

In some applications it may be desirable to have the biomolecule immobilized to the surface as a capture reagent present in a limiting amount. Again the DLC film surface chemistry can be adjusted to restrict the amount of capture reagent immobilized.

The minimum thickness of DLC coated onto a surface to enhance biomolecule attachment has been demonstrated to be in the range of 50-500 Å. However, this does not represent the upper limit. A very thin layer of approximately 5 Å is adequate to provide for a cap of DLC film which will attach biomolecules. This is particularly useful when the DLC is combined with an AR layer in a visual assay device. However, the upper limit may be much higher, in the range of microns, for methods which are dependent on a tracer for signal generation. The surfaces which can be coated include a wide range of configurations, making the attachment of biomolecules to these surfaces through DLC possible. Thus, DLC can be used to immobilize biomolecules in a variety of sensor, electrode, ELISA, RIA, and other bioassay formats.

If the DLC is to be used as both an antireflective layer and attachment layer for an optical immunoassay device it must meet the following criteria. The material to be useful in an interference assay method must have a refractive index near 2.0. DLC has an index of 2 to 3 in the visible spectrum of light with a minor complex index component. This yields a better light output for improved color production. When the complex index is minor there is less absorption of the incident light. The DLC must be optically transparent for some applications. A DLC cap combination with an adjusted layer of an AR film is also suitable for the generation of a visible interference effect. One possible combination would be a 450 Å, $n_f$=2.0, film of silicon nitride with a cap of 50 Å DLC with an $n_f$=1.7. Those of ordinary skill in the art would be able to produce other suitable DLC cap combinations.

Receptive Layer

The analyte specific binding reagent may be a chelator, an antibody, an antigen, a receptor, a ligand, a protein, a nucleic acid, DNA, RNA, enzymes, any biological molecule capable of binding a specific analyte, or analogs or derivatives thereof, and or a polymer layer.

Coating of the binding reagents will be performed by either dipping the substrate in a tank of the reagents or by spraying the reagents on and rinsing the substrate. Spot coating, ink jetting, air brushing, or other techniques may also be used. The reagents once coated, may or may not need to be overcoated with a stabilizing layer for storage purposes.

It is possible to use a non-specific capture mechanism for detection of analyte. In this assay format, the analyte may adhere to the surface through a number of chemical interactions. Once the analyte binds the optical device, a specific reagent is used to detect analyte presence (e.g., an antibody specific for the analyte to which may be attached an additional mass enhancing material).

Polyester or Polycarbonate, Amorphous Silicon, Silicon Nitride and Nickel

A specific, channel containing support will include polyester or polycarbonate material with random channels ranging in size from 0.01-14 micrometers. Channel density of the surface is approximately 1-15% and should be kept below 15% for optimum performance. This prevents a reduction in the effective refractive index of the AR film due to the presence of channels. The channeled support will be coated with amorphous silicon in a thickness range from 300 Å-5000 Å. The thickness and packing density of the base optical layer can be adjusted to control the reflectivity from the base layer. This in turn will govern the overall reflectivity and allow it to be optimized for individual applications. Optical coating materials may be conformal to the channeled support. This is less necessary when an amorphous silicon is used. The channeled support must be relatively uniform. Channel density, although random, must remain approximately the same percentile basis per surface area.

The silicon nitride layer will be reactively deposited on the amorphous silicon layer and may have a range of thickness from 30-70 nm which can be controlled for optimal contrast for a specific application. One advantage of using the vapor phase deposition of the current optical layers is that control of the reflectivity and the contrast as well as color development will allow each surface to be tailored to a specific application. The largest differences in the surface structure will be realized in the automated versus visual versions of the detection scheme.

There are many advantages to using amorphous silicon for the base layer in the device. First, amorphous silicon has a higher refractive index than polycrystalline silicon. Secondly, films of amorphous silicon can be made thinner due to the increased absorption in the visible wavelengths. Third, amorphous silicon can be deposited onto low temperature supports such as paper and plastic because surface heating is not necessary to form amorphous silicon. Amorphous silicon also exhibits excellent binding and mechanical stability over some other high index material.

A thin layer of nickel is preferred for the attachment layer for a number of reasons. First, nickel adheres very well to the AR layers outlined above and especially to silicon nitride. In addition, nickel has a refractive index of 1.78 and although its extinction coefficient is $7.4 \times 10^5$, thin films of the metal do not appreciably affect the reflectivity of the AR layer. The use of nickel seems to increase the overall coverage of biological molecules over the native silicon nitride. This may be due to specific interactions such as hydrogen bonding, pi backbonding and the formation of sulfide linkages to the metal.

EXAMPLES

Example 1

Use of Absorbent Material to Evaluate Flow Characteristics

The flow characteristics of the 0.6, 1, and 5 µm channeled-polycarbonate supports show the desired flow characteristics when backed with cellulose acetate or other fibrous or porous wicking material. Flow characteristics of interest are the flow rate through and/or across the surface, the retention of fluid at the optical surface, and uniform flow of sample solution over entire surface. The flow rate should be selected to allow sufficient reaction time assuming that 160 to 1000 µl of sample will be used. Optimal flow and drying of the surfaces are achieved when the hydrophilic channeled supports are backed with a very thin hydrophobic membrane which is backed with another hydrophilic absorbent material to prevent backflow of the sample as the surface dries. The drying step, while not a necessary step in visualization of the optical signal does produce a signal that is more easily assessed due the lower index of air compared to the fluid matrix (unless the matrix is a gas). This substantially reduces the total assay time.

Example 2

Assay Time Reduction Relative to a Non-Channeled Support

Test surfaces reactive to the polysaccharide antigen specific to group A streptococcus were produced on a non-channeled support (silicon) and a channeled support (polycarbonate). The silicon test device is a commercially available device. The channeled support was a 1 µm channel size polycarbonate which was coated with amorphous silicon followed by silicon nitride and then silylated with DCDMS as in Example 3. Once silylated, the surface was coated with anti-Strep A antibody and modified STREP A OIA® assays were carried out. Antigen was extracted in a 1 minute extraction step. The extraction was neutralized with a reagent which also contains the conjugated anti-Strep A antibody with HRP for precipitation of a solid film forming enzyme product. The complete extraction volume 250 µl (but can be in excess of 300 µl) was applied to the surface of the channeled device. Sample size for the solid non-channeled device is limited to approximately 35 µl. Sample flowed through the surface of the channel device in approximately 30 seconds and was followed by 2 washes of 10 seconds each. The solid non-channel containing device requires a 2 minute incubation step followed by a single wash of approximately 20 seconds. Then the enzyme substrate was applied to the channel-containing optical support for at least 1 minute, potentially for as little as 30 seconds (especially at higher antigen concentrations). The device was then washed and dried prior to visualization. The solid device required a 2 minute incubation with the enzyme substrate prior to the wash, dry, and interpretation. Total reduction in assay time for the channeled-support versus the solid support is 1.5 minutes or approximately half of the total assay time. The channel-containing device with its mass transport/laminar flow of sample gave the same performance level, but increased speed as compared with a standard solid optical support device.

Example 3

Strep A OIA® Assay Comparison

A support of polycarbonate with 1 μm channels was coated with a base optical layer of amorphous silicon to a thickness of 2000 Å. The AR layer was silicon nitride coated to a thickness of 420 Å, refractive index is 2.0. The optical layers were applied by ion beam deposition using industry standard parameters. The attachment layer was DCDMS, 2% in 1,1,1-Trichloroethane which was coated onto the essentially support using a vapor deposition method with no catalyst and for 10 minutes at room temperature. Anti-Strep A antibody was applied by solution coating the device for 2 hours at 45° C. in a solution containing 0.1 M HEPES, pH8.0, 6 μg/ml of antibody. The device was rinsed with deionized water and used immediately. The assay of this device used 360 μl of pre-extracted antigen standard+40 μl of conjugate. The mixture was applied to the optical device and differential pressure (vacuum) applied for 2 minutes for each antigen standard and then 2 washes of approximately 100 μl of water each were conducted. Then substrate was applied for 4 minutes followed by the above described wash procedure. Drying was accomplished by the differential pressure and the visual change was recorded. The channel-containing device when evaluated with this specific antigen preparation demonstrated a cut-off level of 1:96000 with a 400 μl sample. Use of a solid (non-channeled) support device gave a cut-off level of 1:2400 for this antigen preparation. Thus, an increase in sensitivity of about 40 fold is achieved by use of the channel-containing support. Differential pressure was used only to control flow to match the times in the STREP A OIA® assay (non-channel support). The use of differential pressure is not required, as the device will inherently allow for the mass transport/laminar flow of the sample.

In another experiment 300 μl sample of a 1:2400 antigen standard mixed with conjugate was applied to a sample of the channel-containing optical support and the entire volume drawn through in 30 seconds using a differential pressure system. Three sequential washes of 100 μl each for 5 seconds each were conducted. After the rinse, the substrate was applied for 1 minute and 30 seconds. Color development could be observed within 30 seconds of incubation time. A final rinse of 200 μl was passed through the channel-containing optical support for 10 seconds. The total assay time for the channel-containing optical support was 2 minutes and 25 seconds compared to 8 minutes for the solid support (at a cut-off level of 1:2400). It is feasible, based on this data to reduce the assay time using a channel-containing support to 2 minute and 25 seconds while maintaining comparable sensitivity to the solid support system (1:2400 cut-off level), which has been demonstrated to have excellent clinical performance.

Example 4

Comparison of DLC Coated Thin Films with T-Polymeric Siloxane Coated Thin Films Silicon wafers were coated with silicon nitride and then with either T-polymeric siloxane as described in U.S. Pat. No. 5,468,606. The DLC was applied as a 50 Å cap. A number of different DLC coatings were compared to the T-polymeric surface. The various DLC surface lots evaluated in this example were produced by ion beam deposition. The deposition process parameters were varied to produce slightly different DLC coatings. The parameters that can be varied include temperature, coating time, type and amount of carbon containing gas, presence, absence, or amount of non-carbon gas present, and overall chamber pressure. Those skilled in the art known how to vary these and other parameters to alter the characteristics of the DLC surface. In this example DLC was produced by direct ion beam deposition using methane and argon mixtures in DC and inductively coupled Rf ion guns. The methane is broken down in the plasma and deposited on a surface as a hydrogenated amorphous diamond film. Films were produced at approximately 25° C. The temperature of the substrate being coated may also strongly influence the hardness and hydrophobicity of the DLC generated.

The surface energy of hydrogenated amorphous carbon films can be correlated with the hydrophobicity of these films. A carbon film that has a very hydrophilic surface will have a water contact angle of 60° and a surface energy of 49 ergs/cm$^2$, while a hydrophobic surface will have a water contact angle of 110° with a surface energy of 23-24 ergs/cm$^2$.

The films produced in this and other examples have a water contact angle of 71° and a surface energy of 45 ergs/cm$^2$. The amorphous hydrogenated carbon films in this and subsequent examples have a hydrogen content of between 12-23%.

The assay method involved incubating the surface with a volume of sample containing either a 1:1000, a 1:5000, or a negative of LPS antigen derived from Chlamydia elementary bodies. Once the LPS is non-specifically adhered to the DLC or T-polymer surface, an anti-LPS antibody HRP conjugate was allowed to incubate on the surface and incubated for 10 minutes. Then 100 μL of the soluble TMB substrate was removed and placed in a microtiter well containing 100 μL and then the absorbance at 450 nm recorded. This gives a semi-quantitative comparison of the DLC coating and the T-polymer surface capture of LPS. FIGS. 3 and 4 compare the performance of a variety of DLC coatings to the T-polymer surfaces; the value plotted is the signal-noise (negative sample result). At the 1:1000 LPS dilution the signal generated on the DLC surface is comparable to or in some cases higher than the corresponding T-polymer value (see FIG. 3). This indicates that the DLC surface can be successfully modified to attenuate LPS binding to a desired level. The results at the 1:5000 LPS dilution are similar to those observed for the 1:1000 LPS dilution but in some cases the level of binding to DLC is significantly improved (see FIG. 4). In other cases the DLC was significantly less able to capture LPS. Again supporting the ability of the DLC to be tailored to the desired degree of biomolecule retention.

Example 5

Detection of Influenza Virus a or B on DLC Surfaces

A silicon wafer was coated with approximately 450 Å silicon nitride and 50 Å of DLC with a goal of a refractive index of 2.0. Measurements of the composite films thickness indicates that the wafer was coated to a thickness of 493.8±5.8 Å with a refractive index of 2.058±0.003.

Both monoclonal antibodies to Influenza A and Influenza B were applied as a spot of 5 μL of varying antibody concentration (equal amounts of each antibody at stated concentration were in each spot) onto the DLC surface and incubated for 10 minutes, washed, and blotted dry. Then 15

μL of the conjugate (anti-Influenza A and anti-Influenza B conjugated to Horseradish Peroxidase (HRP)) was mixed with 75 μL of diluted virus A or B of varying concentration (based on fold dilution in Table 1). The Influenza A strain used was Hong Kong A (HK A) and the Influenza B strain used was Panama B. A 10 μL sample of this mixture was applied to the surface and incubated for 5 minutes at room temperature. The mixture was rinsed from the surface and blotted dry. Then a drop of HRP substrate was applied to the surface for 5 minutes to allow a precipitate to form. The substrate was washed and then blotted dry. Results are shown in the Table 1. The table compares the amount of antibody applied to the surface versus a negative control of PBS and the capture of HONG KONG (Influenza A strain) or PANAMA (Influenza B strain) at varying dilutions of the two viruses. Good capture of either strain of Influenza was achieved with a surface antibody spot of 5/g (0.005 mL×1 mg/mL×1000 μg/mg).

TABLE 1

| [Ab] Spot (mg/ml) | PBS | 1/10 HK A Virus | 1/10 PN B Virus | 1/100 HK A Virus | 1/100 PN B Virus | 1/250 HK A Virus | 1/250 PN B Virus | 1/500 HK A Virus | 1/500 PN B Virus |
|---|---|---|---|---|---|---|---|---|---|
| 1 | — | 4+ | 4+ | 2+ | 2+ | 1+ | 1+ | — | — |
| 0.5 | — | 4+ | 4+ | 2+ | 2+ | 1+ | 1+ | — | — |
| 0.05 | — | 4+ | 4+ | 2+ | 2+ | 1+ | 1+ | — | — |
| 0.01 | — | 2+ | 2+ | — | — | — | — | — | — |
| 0.005 | — | 2+ | 2+ | — | — | — | — | — | — |

Example 6

Detection of a Ligand on a Receptor Coated Industrial Grade Diamonds

A receptor was immobilized on a 0.2 micron industrial grade diamonds from Key Industrial Diamond Corporation. The receptor was coated onto the diamonds from a 1 mg/ml stock solution: 100 μL volume of receptor was mixed with 10 μL of diamond. The receptor was allowed to incubate over night at room temperature. A 2 μL sample of this material was applied to the surface and incubated for 15 minutes. The solid support was washed with water and dried under a stream of nitrogen. This produced a DLC/receptor coated surface.

To test the functionality of the DLC/receptor surface a 15 μL sample of ligand which will react with the receptor was applied and incubated for 5 minutes. The unbound ligand was rinsed from the surface which was dried under a stream of nitrogen. Then anti-ligand/HRP conjugate was applied for 5 minutes followed by a rinse/dry step. Results were read visually. All positive samples were detected (data not shown). While not optimized, this experiment indicates that industrial diamonds can be used to immobilize biomolecules and then a film coating of the immobilized biomolecule can be created.

Example 7

Capture of DNA on a DLC Surface

A biotinylated 14-mer was diluted to 1 μmole/mL in deionized water. From that stock the 14-mer was diluted down to 10 pmole/mL. A 1 μL aliquot of each dilution was applied to the DLC coated silicon nitride/polyester surface and allowed to dry for 30 minutes. Any unbound 14-mer was washed from the surface with water and the surface dried. Each DNA spot was covered with 100 μL of a anti-biotin-HRP conjugate and incubated for 10 minutes at room temperature followed by a rinse/dry step. The DNA/conjugate spot was then covered with approximately 100 μL of a precipitating TMB substrate and incubated for 5 minutes. Again a rinse/dry step was performed. A positive indication of the capture of DNA onto the DLC surface is visualized by a color change in the applied DNA spot relative to the optical background. This experiment indicated that 10 fmoles of DNA was immobilized on the DLC surface and visualized through the precipitating enzyme reaction (data not shown).

Example 8

Detection of a DNA:DNA Hybrid on DLC Surface

As in previous examples a DLC/silicon nitride/polyester support was used. A 10 nmole aliquot of a biotinylated 14-mer was mixed with a 10 nmole aliquot of a complementary 14-mer. The probes were allowed to anneal for 15 minutes at room temperature in 20 mM Tris, pH 7.5, 15 mM $MgCl_2$, and 50 mM NaCl (final volume 22 μL). Then 4 μL of the hybridization solution was removed and mixed with 1 μL of S1 nuclease, 22 μL of water, and 3 μL of S1 buffer. Digestion of single stranded DNA was allowed to proceed for 15 minutes at room temperature. Then a 1 μL sample of the hybrid was applied to the DLC surface and allowed to dry. The surface was washed and dried. A sample of anti-biotin antibody/HRP conjugate was applied and allowed to incubate 10 minutes, followed by a wash and dry step. Then a sample of HRP precipitating substrate was applied to the surface for 5 minutes. The surface was washed, dried, and visualized. With this technique 60 pmoles of the biotinylated probe was detected (data not shown). No signal was generated in the absence of complement or both probes. Signal could be generated by capture of the biotinylated probe or the hybrid in the absence of S1 nuclease.

Example 9

Control of DLC Film Hydrophobicity

To increase the hydrophobicity of a DLC film more $sp^3$ character may be introduced into the film or the amount of hydrogenated carbon in the DLC film may be increased. In this example the amount of hydrogenated carbon was increased in the DLC film. Ion beam deposition is one of many coating processes that can be employed. A midpoint coating protocol which deposits hydrogenated amorphous DLC at 25 Å/minute incorporates the following settings:

| PARAMETER | SETTING |
|---|---|
| $R_f$ power forward | 300 W |
| $R_f$ reverse | 0 W |

-continued

| PARAMETER | SETTING |
|---|---|
| Beam Voltage | 100 mAmp |
| Acceleration Voltage | 200 V |
| Current Voltage | 8.2 mAmp, constant |
| Grid Temperature | 170° C. |
| Platen Temperature | 85°–90° C. |
| Flow Rate ($CH_4$) | 40 sccm* |
| Source | 8 cm–off |

*standard cubic centimeters/minute

Variations in the hydrophobicity of the DLC film can be made by varying $R_f$ Power Forward in 50 W increments and varying the $CH_4$ flow rate so that a $R_f$ Reverse of zero is maintained. All other parameters are held constant within the normal constraints of the coating chamber. To produce a more graphite like DLC the gas can be changed to a mixture of $CH_4$ and $CH_2CH_2$ or to pure $CH_2CH_2$. A change in the ratio of the two gases using the parameter settings listed above would produce a range of DLC films varying in hydrophobicity. For a pure $CH_2CH_2$ gas the above described parameters setting could also be used. One of skill in the art would understand that other deposition processes could be so modified to produce a range of DLC and based on the above discussion of ion beam deposition, could make such modifications to other deposition processes, such as chemical vapor deposition, plasma deposition, etc.

Other embodiments are within the following claims.

What is claimed is:

1. An optical assay device for the detection of an analyte of interest in a fluid sample comprising:
   a support containing channels;
   an optically functional layer containing channels, said optically functional layer having an optical property of which is detectably altered upon a change in mass on said optically functional layer related to analyte binding, positioned on said support;
   an attachment layer containing channels positioned on said optically functional layer; and
   an analyte specific receptive layer containing channels positioned on said attachment layer,
   wherein said channels in said support, said optically functional layer, said attachment layer and said analyte specific receptive layer are positioned to allow fluid flow from the analyte specific receptive layer to the support.

2. An optical assay device for the detection of an analyte of interest in a fluid sample comprising:
   a support containing channels;
   an optically functional layer containing channels, said optically functional layer having an optical property of which is detectably altered upon a change in mass on said optically functional layer related to analyte binding, positioned on said support; and
   an attachment layer containing channels positioned on said optically functional layer to provide nonspecific capture of said analyte,
   wherein said channels in said support, said optically functional layer and said attachment layer are positioned to allow fluid flow from the attachment layer to the support.

3. An optical assay device for the detection of an analyte of interest in a fluid sample comprising:
   a porous support;
   an optically functional layer, an optical property of which is detectably altered upon a change in mass on said optically functional layer related to analyte binding, comprising discrete, optically functional particles embedded in said support configured and arranged to provide channels through said optically functional layer;
   an attachment layer containing channels positioned on said particles; and
   an analyte specific receptive layer containing channels positioned on said attachment layer,
   wherein said channels in said optically functional layer, said attachment layer and said analyte specific receptive layer are positioned to allow fluid flow from said analyte specific receptive layer to said attachment layer and to said optically functional layer wherein fluid enters pores of said porous support.

4. An optical assay device for the detection of an analyte of interest in a sample comprising:
   a porous support;
   an optically functional layer, an optical property of which is detectably altered upon a change in mass on said optically functional layer related to analyte binding, comprising discrete, optically functional particles embedded in said support configured and arranged to provide channels through said optically functional layer; and
   an attachment layer containing channels positioned on said particles to provide nonspecific capture of said analyte,
   wherein said channels in said optically functional layer and said attachment layer are positioned to allow fluid flow from the attachment layer to said optically functional layer wherein fluid enters pores of said porous support.

5. An optical assay device for the detection of an analyte of interest in a sample comprising:
   a porous support;
   an optically functional layer, an optical property of which is detectably altered upon a change in mass on said optically functional layer related to analyte binding, containing channels positioned on said support;
   an attachment layer containing channels positioned on said optically functional layer; and
   an analyte specific receptive layer containing channels positioned on said attachment layer,
   wherein said channels in said optically functional layer, said attachment layer and said analyte specific receptive layer are positioned to allow fluid flow from said analyte specific receptive layer to said attachment layer and to said optically functional layer wherein fluid enters pores of said porous support.

6. An optical assay device for the detection of an analyte of interest in a sample comprising:
   a porous support;
   an optically functional layer, an optical property of which is detectably altered upon a change in mass on said optically functional layer related to analyte binding, containing channels positioned on said support; and
   an attachment layer containing channels positioned on said optically functional layer to provide nonspecific capture of said analyte,
   wherein said channels in said optically functional layer and said attachment layer are positioned to allow fluid flow from said attachment layer to said optically functional layer wherein fluid enters pores of said porous support.

7. The device of any of claims 1, 2, 3, 4, 5 or 6 wherein said optically functional layer further comprises an antireflective layer.

8. The device of any of claim 1, 2, 3, 4, 5 or 6, wherein said attachment layer is nickel.

9. The device of any of claim 1, 2, 3, 4, 5 or 6, wherein said device further comprises a liquid absorbent material surrounding said optically functional layer or beneath said support.

10. The device of any of claims 1, 2, 3, 4, 5 or 6, wherein said support comprises polyester or polycarbonate,
said optically functional layer comprises a layer of silicon nitride positioned on a layer of amorphous silicon, and
said attachment layer comprises nickel.

11. The device of any of claims 1, 2, 3, 4, 5 or 6 wherein said support comprises polycarbonate or polyester, and
said optically functional layer comprises a layer of germanium on which is positioned a layer of diamond-like carbon.

12. The device of any of claims 1, 2, 3, 4, 5 or 6 wherein said optically functional layer comprises a layer of germanium on which is positioned a layer of diamond-like carbon, and said attachment layer comprises nickel.

13. Method for constructing an optical assay device with laminar flow properties, comprising the steps of:
providing a support comprising channels;
providing an optically functional layer containing channels, said optically functional layer having an optical property of which is detectably altered upon a change in mass on said optically functional layer related to analyte binding, on said support;
providing an attachment layer containing channels on said optically functional layer, and
providing an analyte specific receptive layer containing channels on said attachment layer,
wherein said channels in said support, said optically functional layer, said attachment layer and said an analyte specific receptive layer are positioned to allow fluid flow from the analyte specific receptive layer to the support.

14. Method for constructing an optical assay device with laminar flow properties, comprising the steps of:
providing a support comprising channels;
providing an optically functional layer containing channels, said optically functional layer having an optical property of which is detectably altered upon a change in mass on said optically functional layer related to analyte binding, on said support; and
providing an attachment layer containing channels on said optically functional layer to provide nonspecific capture of said analyte,
wherein said channels in said support, said optically functional layer and said attachment layer are positioned to allow fluid flow from the attachment layer to the support.

15. A composition comprising:
a support comprising channels or a porous support, and an optically functional layer containing channels positioned on said support, said optically functional layer having an optical property of which is detectably altered upon a change in mass on said optically functional layer related to analyte binding;
wherein said channels in said optically functional layer are positioned to allow fluid flow to the support either through channels in the support or via pores in the porous support.

16. The composition of claim 15, wherein said support is porous and said channels in said optically functional layer are formed from optically functional particles.

17. The composition of claim 15, wherein said support is porous.

18. The composition of claim 15, wherein said support comprises polycarbonate and said optically functional layer comprises amorphous silicon.

19. The composition of claim 18, wherein said optically functional layer further comprises a layer of silicon nitride positioned on said amorphous silicon.

20. The composition of claim 15, wherein said support comprises polycarbonate and said optically functional layer comprises germanium.

21. The composition of claim 20, wherein said optically functional layer further comprises a layer of diamond-like carbon positioned on said germanium.

22. The composition of claim 15, wherein said support comprises polyester and said optically functional layer comprises amorphous silicon.

23. The composition of claim 22, wherein said optically functional layer further comprises a layer of silicon nitride positioned on said amorphous silicon.

24. The composition of claim 15, wherein said support comprises polyester and said optically functional layer comprises germanium.

25. The composition of claim 24, wherein said optically functional layer further comprises a layer of diamond-like carbon positioned on said layer of germanium.

26. Method for constructing an optical assay device with laminar flow properties, comprising the steps of:
providing a porous support;
providing an optically functional layer, an optical property of which is detectably altered upon a change in mass on said optically functional layer related to analyte binding, comprising discrete, optically functional particles embedded in said support configured and arranged to provide channels through said optically functional layer;
providing an attachment layer containing channels positioned on said particles; and
providing an analyte specific receptive layer containing channels positioned on said attachment layer,
wherein said channels in said optically functional layer, said attachment layer and said analyte specific receptive layer are positioned to allow fluid flow from said analyte specific receptive layer to said attachment layer and to said optically functional layer wherein fluid enters pores of said porous support.

27. Method for constructing an optical assay device with laminar flow properties, comprising the steps of:
providing a porous support;
providing an optically functional layer, an optical property of which is detectably altered upon a change in mass on said optically functional layer related to analyte binding, comprising discrete, optically functional particles embedded in said support configured and arranged to provide channels through said optically functional layer; and
providing an attachment layer containing channels positioned on said particles to provide nonspecific capture of said analyte,
wherein said channels in said optically functional layer and said attachment layer are positioned to allow fluid flow from the attachment layer to said optically functional layer wherein fluid enters pores of said porous support.

28. Method for constructing an optical assay device with laminar flow properties, comprising the steps of:
   providing a porous support,
   providing an optically functional layer, an optical property of which is detectably altered upon a change in mass on said optically functional layer related to analyte binding, containing channels positioned on said support;
   providing an attachment layer containing channels positioned on said optically functional layer; and
   providing an analyte specific receptive layer containing channels positioned on said attachment layer,
   wherein said channels in said optically functional layer, said attachment layer and said analyte specific receptive layer are positioned to allow fluid flow from said analyte specific receptive layer to said attachment layer and to said optically functional layer wherein fluid enters pores of said porous support.

29. Method for constructing an optical assay device with laminar flow properties, comprising the steps of:
   providing a porous support;
   providing an optically functional layer, an optical property of which is detectably altered upon a change in mass on said optically functional layer related to analyte binding, containing channels positioned on said support; and
   providing an attachment layer containing channels positioned on said optically functional layer to provide nonspecific capture of said analyte,
   wherein said channels in said optically functional layer and said attachment layer are positioned to allow fluid flow from said attachment layer to said optically functional layer wherein fluid enters pores of said porous support.

30. The device of any of claims 1, 2, 3, 4, 5 6, 13, 14, 15 or 21–29 wherein said analyte is selected from the group consisting of antigens, antibodies, receptors, ligands, chelates, proteins, enzymes, nucleic acids, DNA, RNA, pesticides, and herbicides.

31. The device of any of claims 1, 2, 3, 4, 5 6, 13, 14, 15 or 21–29 wherein said optically functional layer comprises a layer of silicon nitride positioned on a layer of amorphous silicon.

32. The device of any of claims 1, 2, 3, 4, 5 or 6, 13, 14, 15 or 21–29 wherein said attachment layer comprises diamond-like carbon.

33. The device of any of claims 2, 4, 6, 14, 27 or 29 wherein said channels in said attachment layer do not exceed 15% of the surface area of the layer.

34. The device of any of claims 2, 4, 6, 14, 27 or 29 wherein said channels in said device are not interconnected.

35. The device of any of claims 1, 3, 5, 13, 26 or 28 wherein said channels in said analyte specific receptive layer do not exceed 15% of the surface area of the layer.

36. The device of any of claims 1, 3, 5, 13, 26 or 28 wherein said channels in said device are not interconnected.

37. The composition of claim 15 wherein said channels in said optically functional layer do not exceed 15% of the surface area of the layer.

38. The composition of claim 15 wherein said channels in said device are not interconnected.

39. The device of any of claims 1-3, 5, and 6, wherein said channels are configured to provide laminar flow of sample across the layer which binds analyte of said support, said flow achieved by the movement of sample into channels that connect the layer which binds analyte to the support.

40. The composition of any of claims 15, 16–25, 37 and 38 wherein said channels are configured to provide laminar flow of sample across the layer which binds analyte of said support, said flow achieved by the movement of sample into channels that connect the layer which binds analyte to the support.

* * * * *